United States Patent
Stürmann et al.

(10) Patent No.: US 6,706,902 B2
(45) Date of Patent: Mar. 16, 2004

(54) CONTINUOUS PROCESS FOR THE SYNTHESIS OF NANO-SCALE PRECIOUS METAL PARTICLES

(75) Inventors: Martin Stürmann, Leverkusen (DE); Markus Weisbeck, Köln (DE); Gerhard Wegener, Mettmann (DE); Frank Zbrozek, Leverkusen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 37 days.

(21) Appl. No.: 10/074,274

(22) Filed: Feb. 12, 2002

(65) Prior Publication Data

US 2002/0115873 A1 Aug. 22, 2002

(30) Foreign Application Priority Data

Feb. 16, 2001 (DE) .......................................... 101 07 777

(51) Int. Cl.[7] .............................. B01J 21/06; B01J 23/38
(52) U.S. Cl. ........................ 549/523; 502/150; 502/158; 502/243; 502/261; 502/262; 502/325; 502/339; 502/344; 502/313; 502/317; 502/350
(58) Field of Search ................................. 502/150, 158, 502/243, 261, 262, 325, 339, 344, 313, 317, 350; 549/523

(56) References Cited

U.S. PATENT DOCUMENTS

| | | | |
|---|---|---|---|
| 5,235,111 A | 8/1993 | Clerici et al. | 469/399 |
| 5,409,876 A | 4/1995 | Clerici et al. | 469/242 |
| 5,410,007 A | 4/1995 | Lewis et al. | 528/15 |
| 5,623,090 A | 4/1997 | Haruta et al. | 568/360 |
| 6,034,028 A | 3/2000 | Hayashi et al. | 827/243 |
| 6,090,961 A | 7/2000 | Hanaoka et al. | 556/11 |
| 6,099,964 A | 8/2000 | Baumann et al. | 428/402 |
| 6,252,095 B1 | 6/2001 | Hayashi et al. | 99/523 |
| 2001/0019774 A1 * | 9/2001 | Suzuki et al. | 428/447 |

FOREIGN PATENT DOCUMENTS

| | | |
|---|---|---|
| DE | 197 09 101 | 9/1998 |
| DE | 199 25 926 | 12/2000 |
| DE | 199 59 525 | 6/2001 |
| DE | 100 23 717 | 11/2001 |
| EP | 1 005 907 | 6/2000 |
| WO | 98/00413 | 1/1998 |
| WO | 98/00414 | 1/1998 |
| WO | 98/00415 | 1/1998 |
| WO | 00/59633 | 11/1999 |
| WO | 00/59632 | 10/2000 |

* cited by examiner

*Primary Examiner*—Tom Dunn
*Assistant Examiner*—Christina Ildebrando
(74) *Attorney, Agent, or Firm*—Joseph C. Gil; John E. Mrozinski, Jr.

(57) ABSTRACT

The present invention relates to the continuous production of nano-scale precious metal particles on SiH-containing support materials, the compositions themselves, and the use of these precious metal-containing compositions as catalyst. The continuous process according to the invention includes impregnating support materials and, after thermal activation, drying the support materials by spraying or by fluidized bed technology leads to form precious metal-containing support compositions that are active in the catalysis of oxidation reactions. The catalytically active precious metal-containing support compositions exhibit high selectivities and productivities and have very long catalyst service lives without deactivation. The invention also relates to a process for the oxidation of hydrocarbons in the presence of oxygen, a reducing agent and the precious-metal containing support compositions of the present invention.

17 Claims, No Drawings

CONTINUOUS PROCESS FOR THE SYNTHESIS OF NANO-SCALE PRECIOUS METAL PARTICLES

The present invention relates to a process for the continuous production of nano-scale precious metal particles on SiH-containing support materials and the use of these precious metal-containing compositions as catalysts. Specifically, the process according to the invention comprises: a) impregnating support materials; b) drying the support material by spraying or by fluidized bed technology leads to form compositions that are after thermal activation active in the catalysis of oxidation reactions. The catalytically active precious metal-containing compositions exhibit high selectivities and productivities and very long catalyst service lives without deactivation. The present invention also relates to a process for the oxidation of hydrocarbons in the presence of oxygen and a reducing agent.

Processes for depositing gold particles on support materials are known. Such methods are disclosed in, for example, U.S. Pat. No. 5,623,090, WO-98/00413-A1, WO-98/00415-A1, WO-98/00414-A1, WO-00/59632-A1, WO-99/43431-A1, and EP-A1-0 827 779. These references discloses the following processes for depositing gold particles on support materials: deposition-precipitation; co-precipitation; impregnation in solution; incipient wetness; colloid processes; sputtering; chemical vapor deposition ("CVD"), physical vapor deposition ("PVD"), and microemulsion. These references also disclose processes relating to heterogeneously catalyzed gaseous phase oxidations of propene to propene oxide with molecular oxygen in the presence of hydrogen.

Preferably, the deposition-precipitation method is used. With this method, gold particles are precipitated from corresponding gold precursor compounds onto inorganic titanium dioxides, preferably anatase, or inorganic titanium dioxide-containing silicon dioxides. Active catalysts can be obtained by impregnating purely inorganic silicon dioxide surfaces with titanium precursor compounds in solution followed by gold coating by deposition-precipitation and subsequent calcination in an air atmosphere of the resultant materials. These active catalysts nonetheless have relatively low propene conversions, deactivate extremely rapidly (typical half-life times are 10–100 hrs.) and thus cannot be used in large-scale industrial operations.

A disadvantage of the deposition-precipitation process is the fact that the process uses large amounts of solvents. Additionally, a pH adjustment to 7.5–10, using bases, is necessary. Only a fraction of the gold compound used is deposited as catalytically active species on the support material. In addition, production is carried out batchwise and, especially when catalyst supports based on silicon dioxide are used, results in undesirable broad particle size distributions of the precious metal (4 to >>50 nm). Such precious metals must then be precipitated on the support matrix. Typically, only gold particles of <10 nm are catalytically active. The deposition-precipitation method, therefore, is not an efficient process for generating gold particles of a catalytically active size.

Incipient wetness and solvent impregnation methods for generating precious metal particles on support materials carrying SiH groups are disclosed in DE 199 59 525 and DE 100 23 717. The expression "incipient wetness" is used to refer to the process of adding a solution containing soluble gold and/or silver compounds to a support material (impregnation), the volume of the solution on the support being less than, equal to or slightly higher than the pore volume of the support. The solution is rapidly removed after impregnation. DE 199 59 525 and DE 100 23 717, however, do not disclose details of the advantageous limits of the contact times during the coating of the support material.

WO-00/59633-A1 discloses a process for the synthesis of gold particles on support materials. In this reference, inorganic support materials are impregnated with a soluble reducing agent and then with a gold precursor compound. Reducing agents such as acetic acid, lactic acid, citric acid, acetates, alcohols or amines are disclosed.

The catalysts produced according to WO-00/59633-A1 exhibit relatively low activities in the gaseous phase oxidation of hydrocarbons in the presence of hydrogen. Catalysts produced in this way deactivate relatively quickly over reaction time and have broad gold particle size distributions on the support materials.

DE-A1-197 09 101 and EP-A1-0 469 662 disclose a method for the production of gold or precious metal-containing titanium silicalites. The titanium silicalites are impregnated with a gold solution or precious metal compound and then dried. The need to restrict the impregnation time and the influence on the size of the metal particles is not disclosed. Also, the supports of these references do not contain any SiH groups.

The known processes for preparing catalyst preparation are thus extremely unsatisfactory with regard to the methods used for the production of the nano-scale precious metal particles. Additionally, huge reactors are required for industrial processes using relatively inactive catalysts. Also, short catalyst service lives lead to production breakdowns during the regeneration phase or require redundant, costly production paths.

One object of the present invention is to provide an industrial process for the continuous production of nano-scale precious metal particles having homogeneous size distributions on a support material.

Another object of the present invention is to develop new catalysts for the oxidation of hydrocarbons, wherein the precious metal content should be the minimum amount necessary to achieve high catalyst activity. A further object of the present invention is to provide a catalyst available on an industrial scale for the oxidation of alkenes.

Yet a further object of the present invention is to eliminate disadvantages of the known processes for the production of nano-scale metal particles on support materials.

These objects are achieved by using a process wherein support materials comprising precious metal particles having a diameter in the range from 0.01–10 nm are produced by bringing a support material which has SiH groups into contact with at least one precious metal compound and/or precious metal particles for a time span of less than 2 hours and then immediately drying the drying the support material.

Precious metals useful in the present invention include gold, silver or mixtures of gold and silver, palladium, platinum or ruthenium. Preferably, gold is used in the process. Several precious metals may be used simultaneously in the process.

The size distribution of the precious metal particles obtained by the process according to the invention is very narrow. 50% of the particles, preferably 60% of the particles and most preferably 65% of the particles are smaller than 10 nm.

Support materials useful in the invention are purely inorganic materials or organic-inorganic hybrid materials. Preferably, organic-inorganic hybrid materials (hybrid support materials) are used. Amorphous as well as crystalline support materials are also suitable for use in the invention.

The composition of the support materials according to the invention may vary widely. In one preferred embodiment of the invention, the support materials are based on silicon oxide and/or silicon dioxide.

Organic-inorganic hybrid materials useful in the invention are organically modified glasses that preferably form soluble precursor compounds in sol-gel processes via hydrolysis and condensation reactions and that contain non-hydrolysable terminal and/or bridging organic groups in the network. These materials and their production are disclosed, for example, in DE 199 59 525 and DE 100 23 717.

The organic-inorganic and inorganic support materials containing SiH units are preferably produced via sol-gel processes. This is carried out for example by mixing suitable, soluble compounds, the hydrolysis and condensation reaction being initiated by adding water and optionally catalysts (e.g. acids, bases and/or organometallic compounds and/or electrolytes and/or ultrasound catalysis). The implementation of such sol-gel processes is known to the skilled artisan. The sol-gel process is based on the polycondensation of hydrolysed, colloidally dissolved metal component mixtures (sol) with the formation of a network (gel). The use of templates leads to the formation of defined pore structures. The type of template is not restricted.

Hybrid support materials containing a proportion of free silicon-hydrogen units incorporated and/or deposited in the sol-gel network can be prepared in an advantageous manner from titanium and silane precursor compounds. Examples of such silane precursor compounds are monoalkoxysilanes with 1 to 12 carbon atoms, dialkoxysilanes with 1 to 12 carbon atoms, trialkoxysilanes with 1 to 12 carbon atoms, dialkoxymonohalogenated silane with 1 to 12 carbon atoms, monoalkoxydihalogenated silane with 1 to 12 carbon atoms, methylhydrocyclosiloxane, trihalogenated silane, dihalogenated silane, and monohalogenated silane. In addition to low molecular weight precursor compounds, oligomeric and polymeric silicon-hydrogen-containing precursor compounds may be used. Examples of such oligomeric and polymeric silicon-hydrogen-containing precursor compounds are poly(methylhydrosiloxanes), poly(dimethylhydro-siloxaneco-methylhydrosiloxanes) terminated with for example hydride or trimethylsilyl, 1,1,3,3-tetramethyldisiloxane, 1,3,5,7-tetramethylcyclotetrasiloxane, tri-n-hexylsilane and triphenylsilane.

Titanium precursor compounds useful in the present invention include tetraalkoxy titanates with $C_1$–$C_{12}$ alkyl groups such as iso-butyl, tert.-butyl, n-butyl, i-propyl, n-propyl, ethyl or titanium alkoxy complexes as described in U.S. Pat. No. 6,090,961, e.g. ($\eta$5-tetramethylcyclopentadienyl)3-tert.-butyl-5-methyl-2-phenoxy) dimethylsilyl-titanium dimethoxide, or other organic titanium species such as titanyl acetylacetonate, dicyclopentadienyl titanium dihalide, titanium dihalide dialkoxide, titanium halogenated trialkoxide, and titanium siloxanes such as diethoxysiloxane-ethyl-titanate copolymer, available from Gelest Inc.

Preferred halogen substituents are chlorine and/or fluorine. Mixed alkoxides of titanium with other elements, such as titanium triisopropoxy-tri-n-butyltin oxide, may also be used. Titanium precursor compounds may also be used in the presence of complex-forming components such as, for example, acetylacetone or ethyl acetoacetate. Titanium may be bonded to silicon via heterosiloxane bonds.

The support materials may contain, in addition to titanium and/or silicon, metals of Group III, IV, V, VIII, XIII, XIV or XV, of the Periodic System according to IUPAC (1985). Yttrium is the preferred metal from the Group III metals, while zirconium is the preferred metal from Group IV. Examples of the Group V metals include vanadium, niobium and tantalum, with tantalum and niobium being preferred. Iron is the preferred metal from Group VIII, while aluminum, boron, and thallium are preferred metals from Group XIII. Germanium is the preferred metal from Group XIV antimony is the preferred metal from Group XV.

Promoters can also be used in the present invention. Such promoters are usually present in oxide form. Oxides useful in the present invention include those selected from the group consisting of molybdenum, vanadium, scandium, germanium, aluminium, boron, zirconium or mixtures thereof.

The promoters are typically present in dispersed form in the support materials. The chemical composition of these materials may vary over wide ranges. The amount of promoter to silicon oxide is in the range of about from 0–12 mole %, preferably 0–4 mole %. Several different promoters may be used. For hybrid support materials, the promoters are preferably used in the form of promoter precursor compounds soluble in the respective solvent, such as promoter salts and/or promoter-organic compounds, and/or promoter-organic-inorganic compounds. The choice of the promoter precursor compounds is not restricted. Preferred promoter precursor compounds are soluble metal compounds such as nitrates, halides, acetylacetonates, or acetates.

These promoters may increase both the catalytic activity of the composition as well as the service life of the composition in catalytic oxidation reactions of hydrocarbons.

Support materials useful in the present invention have a surface area of at last 0.01 $m^2/g$, preferably in the range of from about 0.1–700 $m^2/g$.

The support materials may be microporous and/or mesoporous and/or macroporous. Although purely microporous systems are suitable, mixed-pore systems of micropores and mesopores are preferred. A proportion of macropores does not as a rule have any negative influence.

Also suitable are support materials having a modified surface. The term "modified surface" within the scope of the invention means that the proportion of the surface hydroxyl groups has been reduced by covalent bonding or coordination bonding of groups selected from the group consisting of silicon-alkyl, silicon-aryl, fluorine-containing alkyl and/or fluorine-containing aryl groups.

Most preferred are organic-inorganic hybrid materials having a modified surface.

In one embodiment of the present invention a solution, suspension or dispersion of the precious metal compound and/or precious metal particles is brought into contact, in an inorganic or organic solvent, with the support material (impregnation of the support materials). Preferably, inorganic solvents such as water are used for hydrophilic support materials, while organic solvents such as alcohols (e.g. methanol, ethanol), ketones, ethers, etc. are used for hydrophobic support materials, such as, for example, hybrid materials. Mixtures of inorganic and organic solvents may also be used.

The impregnation of the support materials is preferably carried out for a specifically defined time. Depending on the nature of the support material (polarity, reduction potential and surface), the impregnation lasts less than 2 hours, preferably less than 1 hour, and more preferably less than 0.5 hour. Impregnation for only a short time will be referred to as "short-time impregnation". In a preferred embodiment of the present invention, impregnation times of less than ten minutes, preferably less than one minute, are used.

The short-time impregnation of the support materials may be carried out in any suitable vessel. The short-time impregnation with a solution, a suspension or a dispersion of the precious metal compounds and/or particles is preferably carried out in a tubular reactor. In order to effect a better mixing in the tubular reactor, fixed mixing elements are used. A defined residence time (which decisively influences the impregnation time) can be used in the present invention. The residence time is less than 2 hours, preferably less than 0.5 hour, and more preferably less than 20 minutes.

In a preferred embodiment of the present invention, the short-time impregnation is carried out continuously by mixing a stream A, which, for example, comprises a support material solution/suspension, with a stream B, which, for example, comprises a solution or dispersion of the precious metal compound or precious metal particles, following which the overall combined stream of A and B flows through a previously designated tubular section, preferably provided with fixed mixing elements, in order to achieve optimum residence time. Stream B may also contain a solvent-free precious metal compound or a precious metal colloid, optionally in a solvent.

The manner in which stream A and stream B are mixed is not fixed. Nozzles may also be used in order to improve the mixing. In one embodiment of the present invention, a jet disperser is used for mixing stream A and stream B. Other methods of mixing, such as, for example, by stirring, ultrasound, etc. can also be used in the present invention.

After the intensive mixing of stream A with stream B and after a defined residence time, the solvent is removed.

In the process according to the present invention, it is necessary to remove the solvent rapidly after a defined residence time. The overall residence time of the solvent is less than 10 minutes, preferably less than 5 minutes and most preferably less than 2 hours. All known methods for removing solvents, such as, for example, vacuum application, large amounts of gas, temperature, filtration, etc. may be used in the present invention.

In a preferred embodiment of the present invention, spray drying technology or fluidized bed technology is used to remove the solvent. The solvent can then be removed sufficiently, rapidly and smoothly after a specific residence time.

Depending on the technology used to remove the solvent, the precious metal-containing support materials may be converted into precious metal-containing fine powders or into more dust-free and better flowable materials. By means of these drying technologies there may be obtained, inter alia, fine powders, fine granules and/or fine agglomerates.

The compositions produced by spray drying and/or fluidized bed technology have uniform properties such as residual moisture, bulk density, flowability, compressibility, etc.

The nature of the gas streams that are used for the drying according to the spray drying and/or fluidized bed technologies is not restricted. Preferably the drying is carried out in the presence of air and/or inert gas atmospheres and/or inert gas streams. Particularly advantageous is the use of inert gases such as nitrogen, helium, argon or mixtures thereof. Also hydrogen or a mixture of hydrogen and inert gases may be used to remove the residual moisture.

The temperatures used in the spray drying and/or fluidized bed drying are also not restricted. Temperatures below 600° C., preferably below 300° C., particularly preferably in the range from 100° to 280° C., are advantageous.

In one embodiment of the present invention the process may also be carried out several times in succession. New precious metal particles are thus generated in each throughput.

The support materials may be activated further before and/or after the precious metal coating, by thermal treatment in a temperature range from 100° to 1200° C. in various atmospheres and/or gas streams, such as air, oxygen, nitrogen, hydrogen, carbon monoxide or carbon dioxide.

In a preferred embodiment of the present invention the thermal activation is carried out at 120° to 600° C. in air or in oxygen-containing gases such as oxygen, or oxygen-hydrogen and/or oxygen-noble gas mixtures or combinations thereof.

The thermal activation is preferably carried out however in the range from 120° to 1200° C. in inert gas atmospheres or streams such as nitrogen and/or oxygen and/or noble gases and/or methane or combinations thereof.

The activation of the precious metal-containing compositions obtained in the process according to the invention is preferably carried out under inert gases in the temperature range from 150° to 600° C.

It may however also be advantageous to treat the support materials free of precious metals thermally at temperatures in the range from 200° to 1200° C. and then coat these support materials with precious metal and finally retreat them thermally at 150° to 600° C. Depending on the activation temperature that is chosen, chemical processes alter the structure of the compositions according to the invention. Thus, for example, the organic-inorganic hybrid compositions after the thermal treatment may contain silicon oxycarbide units. The thermally activated compositions frequently exhibit a significantly higher catalytic activity and a longer service life compared to known catalysts.

The process according to the invention can also be used advantageously with SiH-free support materials to generate metal particles and/or metal oxide particles in the lower nano-scale range.

The present invention also provides the precious metal-containing compositions obtainable in the process according to the invention, characterized in that the composition contains SiH groups and precious metal particles on a support material, with more than 50% of the precious metal particles having a diameter of less than 10 nm.

Preferably 55% and more preferably 60% of the precious metal particles have a diameter of less than 10 nm.

Furthermore, 50% of the precious metal particles preferably have a diameter of less than 9 nm, and more preferably 50% of the precious metal particles have a diameter of less than 8 nm.

The compositions according to the invention contain precious metal particles having a diameter of less than 10 nm on a preferably organic-inorganic hybrid support material. The precious metal is frequently present as elementary particles (analysis by X-ray absorption spectroscopy). Precious metal fractions may also be present in a higher oxidation state, as in precious metal ions or charged clusters. Judging by TEM images, a large proportion of the existing precious metal is present on the outer and inner surface of the support material. This precious metal is preferably in the form of neutral and/or charged precious metal clusters in the nanometer range. Preferably, the gold particles have a diameter in the range from 0.3 to 10 nm, more preferably 0.9 to 9 nm, and most 1.0 to 8 nm. Preferably, the silver particles have a diameter in the range from 0.5 to 50 nm, more preferably 0.5 to 20 nm, and most 0.5 to 15 nm.

The compositions according to the invention may, in the dry state, be described approximately by the following empirical general formula (I) (the residues formed on the surface after modification and possibly incompletely reacted groups are disregarded here).

$$SiO_x.Org.SiH.TiO_{y'}.MoO_{y''}.Mo_z.E \quad (I)$$

wherein $SiO_x$ denotes silicon oxide

Org denotes the non-hydrolysable organic constituents preferably formed in the sol-gel process from the organic-inorganic precursors SiH denotes the molar proportion of SiH units $TiO_{y'}$ denotes titanium dioxide, preferably titanium-silicon heterosiloxane species $MoO_{y''}$ denotes molybdenum oxide M is a promoter, preferably oxides of Ta, Fe, Sb, V, Nb, Zr, Al, B, Ti, Y, Ge or combinations thereof E denotes precious metal (gold and/or silver and/or palladium and/or platinum and/or ruthenium) and x, y', y" and z denote the amount of oxygen necessary to satisfy the valencies of the organic-inorganic and/or purely inorganic elements Si, Ti, Mo and M.

The precious metal-containing composition (I) identified above can vary over wide ranges.

Referred to silicon oxide the proportion of Org in mole % may be between 0 and 200%. The proportion is preferably between 5 and 200%, more preferably between 10 and 100%. The molar proportion of SiH units, referred to silicon oxide, may vary between 0.01 and 100 mole %. Preferably the proportion is between 0.05 and 80%, more preferably between 0.1 and 50 mole %. The proportion of titanium oxide referred to silicon oxide is between 0 and 20 mole %, preferably between 0.3 and 8.0%, most preferably between 0.5 and 6.0%. The proportion of molybdenum oxide referred to silicon oxide is between 0 and 20 mole %, preferably between 0.05 and 7.0%, more preferably between 0.05 and 5.0%. The proportion of $MO_z$ referred to silicon oxide is between 0 and 12 mole %. The proportion of E referred to the precious metal-free composition is between 0.001 and 20 wt. %. The gold concentration should be in the range from 0.001 to 4 wt. %, preferably 0.001 to 2 wt. %, and more preferably from 0.005 to 1.5 wt. % of gold. The silver concentration should be in the range from 0.005 to 20 wt. %, preferably 0.01 to 15 wt. %, and more preferably from 0.02 to 10 wt. % of silver.

Preferred compositions on organic-inorganic hybrid support materials contain between 0 and 20 mole % of titanium based on the amount of silicon oxide, preferably between 0.5 and 10 mole %, particularly preferably between 0.8 and 8 mole %. The titanium is more present in oxide form and is preferably chemically homogeneously incorporated in or bound to the organic-inorganic hybrid material via Si—O—Ti bonds.

It is advantageous if the precious metal particles that are present predominantly have diameters of less than 10 nm and are thus active in oxidation reactions of hydrocarbons. Precious metal particles with diameters of more than 10 nm are less catalytically active and are thus frequently ineffective. Accordingly, conventional catalysts contain more precious metal particles than is actually necessary. The compositions according to the invention, however, contain only slightly more than the minimum necessary amount of precious metal.

The present invention also provides for the use of the compositions as catalysts, in particular in a process for the oxidation of hydrocarbons.

The precious metal-containing compositions according to the invention may be used as catalysts for the partial oxidation of hydrocarbons in the presence of oxygen and a reducing agent. In this regard, identical or even higher catalyst productivities and service lives are achieved compared to the compositions disclosed in DE 199 59 525 and DE 100 23 717.

The compositions described in the present application may be coated with precious metal particles in a continuously operating process. As a result, the compositions according to the invention may be produced in arbitrary amounts. Such is not the case with the compositions disclosed in DE 199 59 525 and DE 100 23 717.

In the catalytic oxidation of hydrocarbons, e.g. propene, in the presence of hydrogen water is always formed as a coupling product with the corresponding selective oxidation product. Water may, however, also be formed under the reaction conditions by the direct oxidation of hydrogen. The precious metal-containing compositions according to the invention substantially prevent the undesired direct combustion of hydrogen to water and thus reduce the consumption of an unnecessarily large amount of hydrogen.

The term hydrocarbon is understood to mean unsaturated or saturated hydrocarbons such as olefins or alkanes, which may also contain heteroatoms such as N, O, P, S or halogens. The organic component to be oxidized may be acyclic, monocyclic, bicyclic or polycyclic, and may be monoolefinic, diolefinic or polyolefinic. With organic components containing two or more double bonds the double bonds may be present in conjugated and non-conjugated form. Preferably, hydrocarbons are oxidized from which those oxidation products are formed whose partial pressure is sufficiently low to enable the product to be continuously removed from the catalyst. Preferred are unsaturated and saturated hydrocarbons with 2 to 20, preferably 2 to 20 carbon atoms, in particular ethene, ethane, propene, propane, isobutane, isobutylene, 1-butene, 2-butene, cis-2-butene, trans-2-butene, 1,3-butadiene, pentenes, pentane, 1-hexene, hexenes, hexane, hexadiene, cyclohexene and benzene.

The supported compositions may be used in any suitable physical form, e.g. ground powder, spherical particles, fine agglomerates, pellets, extrudates, fine granules, granules, etc.

The precious metal-containing compositions according to the invention may be used at temperatures of greater than 20° C., preferably in the range from 80° to 250° C., more preferably in the range from 120° to 215° C. At the high temperatures, steam may be generated as an energy carrier in coupled units. Under appropriate process conditions, the steam may be utilized in the working-up of the product.

Preferably, the gaseous phase reaction is carried out at elevated reaction pressures. Preferred are reaction pressures of greater than 1 bar, more preferably 2 to 50 bar.

The catalyst load may be varied within wide ranges. Preferably, catalyst loads of 0.5–100 l of gas per gram of catalyst and per hour are employed, more preferably 2–50 l of gas per gram of catalyst.

A preferred use is the gaseous phase reaction of oxygen with hydrocarbons in the presence of hydrogen and the precious metal-containing composition according to the invention. In this case epoxides are selectively obtained from olefins, ketones from saturated secondary hydrocarbons, and alcohols from saturated tertiary hydrocarbons. The catalyst residence times are a few weeks, months or even longer depending on the educt that is employed.

The relative molar ratio of hydrocarbon, oxygen, hydrogen and, optionally, a diluent gas may be varied within wide ranges.

The molar amount of the hydrocarbon that is used in relation to the overall molar amount of hydrocarbon, oxygen, hydrogen and possibly diluent gas may be varied within wide ranges. Preferably, an excess of hydrocarbon is employed, referred to the oxygen that is used (on a molar basis). The hydrocarbon content is typically greater than 1 mole % and less than 96 mole %. Preferably, hydrocarbon content in the range from 5 to 90 mole %, more preferably from 20 to 85 mole %, are employed.

The oxygen may be used in a very wide variety of forms, e.g. molecular oxygen, air and nitric oxide. Molecular oxygen is preferred. The molar proportion of oxygen in relation to the overall molar amount of hydrocarbon, oxygen, hydrogen and diluent gas may be varied within wide ranges. Preferably, oxygen is used in molar excess relative to the hydrocarbon. Preferably, oxygen is used in a range from 1–30 mole %, more preferably 5–25 mole %.

In the absence of hydrogen, the supported compositions according to the invention exhibit only a slight activity and selectivity. Up to 200° C. the productivity in the absence of hydrogen is very low, while at temperatures greater than 220° C. relatively large amounts of carbon dioxide are formed in addition to partial oxidation products. Any known source of hydrogen may be used, such as, for example, pure hydrogen, hydrogen from cracking processes, synthesis gas or hydrogen from the dehydrogenation of hydrocarbons and alcohols. In another embodiment of the present invention the hydrogen may also be produced in situ in an upstream reactor, e.g. by dehydrogenation of propane or isobutane or alcohols such as for example isobutanol. The hydrogen may also be introduced into the reaction system as a complex-bound species, e.g. catalyst-hydrogen complex. The molar ratio of the hydrogen fraction—in relation to the overall molar amount of hydrocarbon, oxygen, hydrogen and diluent gas—may be varied within wide ranges. Typical hydrogen contents are greater than 0.1 mole %, preferably 2 to 80 mole %, more preferably 3 to 70 mole %.

Together with the absolutely necessary educt gases described above, there may optionally also be used a diluent gas such as nitrogen, helium, argon, methane, carbon dioxide, carbon monoxide or similar gases that behave largely inertly. Mixtures of these inert components may also be used. The addition of the inert component is often favorable for the transportation of the heat released by the exothermic oxidation reaction and for safety reasons. If the process according to the invention is carried out in the gaseous phase, then, preferably, gaseous diluent components such as, for example, nitrogen, helium, argon, methane and, possibly, steam and carbon dioxide are used. Although steam and carbon dioxide are not completely inert, nevertheless they often have a positive effect at low concentrations (less than 2 vol. %).

When the invention is carried out in the liquid phase, an oxidation-stable and thermally stable inert liquid is expediently chosen (e.g. alcohols, polyalcohols, polyethers, halogenated hydrocarbons, silicone oils). The supported compositions according to the invention are, however, also suitable in the liquid phase for the oxidation of hydrocarbons. Both in the presence of organic hydroperoxides (ROOH) olefins, for example, in the liquid phase are selectively converted on the catalysts to epoxides and, also in the presence of hydrogen peroxide or in the presence of oxygen and hydrogen, olefins in the liquid phase are converted selectively on the catalysts to epoxides.

We have found that the above-described selective oxidation reaction above has a large catalyst-structure sensitivity. With the presence of nano-dispersed gold and/or silver particles on/in the supported composition, there is an increase in the productivity with respect to the selective oxidation.

The properties of the support can also be influenced by incorporating oxophilic elements other than silicon, such as boron, aluminium, yttrium, tantalum, zirconium or titanium. The choice of these heteroatoms is restricted according to the invention to elements that have redox-stable oxidation states.

The spatially narrow interplay of gold and/or silver and titanium and/or molybdenum centres on the support material operates particularly efficiently, i.e. excellent epoxidation catalyst are obtained in the presence of oxygen and hydrogen. The compositions according to the invention can be produced without any technical problems and inexpensively on an industrial scale.

We have surprisingly found that the compositions according to the invention for the catalytic oxidation of alkenes and alkanes have a catalytic activity that is higher by several orders of magnitude, and also have high catalyst service lives, compared to the hitherto known catalyst systems.

The catalysts, which are only slightly deactivated after months of use, can often be regenerated both thermally with oxygen-containing gases or with inert gases at a temperature between 200° and 500° C., as well as by washing and/or extraction with suitable solvents, such as e.g. alcohols, acetone, toluene, DMSO, water, water-surfactants or with dilute hydrogen peroxide solutions (e.g. 3–10% $H_2O_2$ aqueous solution or aqueous-alcoholic solution).

The characteristic properties of the present invention are illustrated in the following examples with the aid of catalyst preparations and catalyst test reactions.

It is understood of course that the invention is not restricted to the following examples.

EXAMPLES

Procedure for Testing the Catalysts (Test Procedure)

A metal tubular reactor of 10 mm internal diameter and 20 cm long was used and was thermostatically controlled by means of an oil thermostat. The reactor was supplied with educt gases from a set of four mass flow regulators (hydrocarbon, oxygen, hydrogen, nitrogen). For the reaction, 500 mg of catalyst were added to the reactor at 160° C. and 3 bar. The standard catalyst loading was 3 l of gas/(g cat.×hr.). Propene for example was chosen as "standard hydrocarbon". In order to carry out the oxidation reaction a gas stream, hereinafter always termed "standard gas composition", was chosen: $C_3H_6/H_2/O_2/:60/30/10\%$. The reaction gases were quantitatively analysed by gas chromatography. The individual reaction products were separated by gas chromatography by means of a combined flame ionization detector ("FID")/WLD method in which the reaction mixture flowed through three capillary columns:
FID: HP-Innowax, 0.32 mm internal diameter, 60 m long, 0.25 μm layer thickness.
WLD: the following units were connected in series
HP-Plot Q, 0.32 mm internal diameter, 30 m long, 20 μm layer thickness
HP-Plot molecular sieve 5 A, 0.32 mm internal diameter, 30 m long, 12 μm layer thickness.

Example 1

This example describes the preparation of a catalyst composed of a silicon-containing and titanium-containing, organic-inorganic hybrid material with SiH units that was coated with gold particles (0.05 wt. %) via a combination of short-time impregnation and spray drying. The contact time (impregnation time) between the gold precursor solution and the support material was 50 seconds.

38 g of a 0.1N solution of p-toluenesulfonic acid in water were added to 245 g of methyl trimethoxysilane (1798 mmole) and 120 g of methanol (analysis purity) and the mixture was stirred for 1 hour. 22 g of tetrabutoxytitanium were then added, the mixture was stirred for a further 10 minutes, a solution of 33 g of triethoxysilane was added, the mixture was restirred for 10 minutes, a mixture of 18 g of a 0.1N solution of p-toluenesulfonic acid in water was added while stirring, and the reaction mixture was finally left to stand. The batch reaches the gel point after ca. 6 minutes. After an ageing time of 12 hours the gel was ground in a mortar and dried for 8 hours at 120° C. in air.

A solution of 0.5 g of 30% $HAuCl_4.3 H_2O$ in 1 l of methanol was placed in a vessel. A suspension of 150 g of titanium-containing hybrid support material in 1 l of methanol was placed in a second vessel and stirred. The support suspension and the gold precursor solution were continuously withdrawn from these vessels and combined in a tube and pumped to the nozzle of a spray dryer. The tube contained static mixing elements. The residence time between the combination of the suspension and solution of the gold compound and the entry to the spray drier was 50 seconds. The temperature of the nitrogen stream in the spray dryer was 130° C.–150° C. The colorless powder that collected at the outlet of the spray dryer had a residual moisture of 2.1%. The coating was 0.032 wt. % of gold on the surface. The gold particles on the surface of the support material had a narrow particle size distribution. The gold particles had a diameter of 2 to at most 10 nm.

The powder was then heated for 4 hours at 400° C. under nitrogen.

According to the test procedure 500 mg of catalytically active gold-containing composition was used as catalyst. A constant PO selectivity of 95% was reached. The catalyst productivity of 150 g of g PO/(kg hybrid material×hr.) which was reached after 8 hours, fell after 10 days to 140 g PO/(kg hybrid material×hr.).

Example 2

This example describes the preparation of a catalyst composed of a silicon-containing and titanium-containing organic-inorganic hybrid material with free SiH units that was coated with gold particles (0.05 wt. %) via a combination of short-time impregnation and spray drying. The contact time between the gold precursor solution and the support material was 13 seconds.

The synthesis of the support material and the subsequent continuous synthesis of fine gold particles was carried out in a similar manner to Example 1, except that in the combination of short-time impregnation and spray drying the residence time between the confluence of the suspension and solution of the gold compound and entry to the spray drier was 13 seconds. The coating on the surface was 0.026 wt. % of gold. The gold particles on the surface of the support material had a diameter of at most 10 nm.

The powder was then heated for 4 hours at 400° C. under nitrogen.

According to the test procedure 500 mg of catalytically active gold-containing composition was used as catalyst. A constant PO selectivity of 95% was achieved. The catalyst productivity of 135 g PO/(kg hybrid material×hr.), which was reached after 7 hours, fell after 10 days to 130 g PO/(kg hybrid material×hr.).

Example 3

This example describes the preparation of a catalyst consisting of a silicon-containing and titanium-containing, organic-inorganic hybrid material with free SiH units, which was coated with gold particles (0.05 wt. %) via a combination of short-time impregnation and spray drying. The temperature of the nitrogen stream in the spray drier was 200° C.

The synthesis of the support material and the subsequent continuous synthesis of fine gold particles was carried out in a similar manner to Example 2 except that in the spray drier the temperature in the nitrogen stream was 200° C. The powder was then heated for 4 hours at 400° C. under nitrogen.

According to the test procedure, 500 mg of catalytically active gold-containing compositions were used as catalyst. A constant PO selectivity of 95% was reached. The catalyst productivity of 160 g PO/(kg hybrid material×hr.), which was reached after 9 hours, fell after 10 days to 140 g PO/(kg hybrid material×hr.).

Example 4

This example describes the preparation of a catalyst composed of a titanium silicalite TS 1, which was coated with gold particles (0.05 wt. %) via a combination of short-time impregnation and spray drying. The contact time between the gold precursor solution and the support material was 60 seconds.

The synthesis of the TS 1 was carried out in a similar manner to U.S. Pat. No. 4,410,501. The generation of the nano-scale gold particles was carried out in a similar manner to Example 3 except that the contact time between the gold precursor solution and the support material up to the nozzle of the spray drying was 60 seconds.

According to the test procedure, 500 mg of catalytically active gold-containing TS 1 was used as catalyst. A constant PO selectivity of 94% was reached. The catalyst productivity of 80 g PO/(kg gold-containing TS 1×hr.), which was reached after 2 hours, fell after 24 hours to 60 g PO/(kg gold-containing TS 1×hr.), after a further 24 hours to 45 g PO/(kg gold-containing TS 1×hr.), and after yet a further 24 hours, to 30 g PO/(kg gold-containing TS 1×hr.).

Example 5

This example describes the preparation of a catalyst composed of an SiH-containing TS 1 analogue, which was coated with gold particles (0.05 wt. %) via a combination of short-time impregnation and spray drying. The contact time between the gold precursor solution and the support material was 60 seconds.

The synthesis of the TS 1 was carried out in a similar manner to U.S. Pat. No. 4,410,501, except that the support material contains in addition 2 mole % of SiH (triethoxysilane as precursor). The generation of the nano-scale gold particles is carried out in a similar manner to Example 4.

According to the test procedure 500 mg of catalytically active gold-containing TS 1 were used as catalyst. A constant PO selectivity of 94% was reached. The catalyst productivity of 100 g PO/(kg Au-containing and SiH-containing TS 1×hr.), which was reached after 3 hours, fell after 24 hours to 90 g PO/(kg Au-containing and SiH-containing TS 1×hr.), after a further 24 hours to 85 g PO/(kg Au-containing and SiH-containing TS 1×hr.), and after yet a further 48 hours, to 48 g PO/(kg Au-containing and SiH-containing TS 1×hr.).

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

We claim:

1. A precious metal-containing support of the formula (I):

$$SiO_x \cdot Org \cdot SiH \cdot TiO_{y'} \cdot MoO_{y''} \cdot Mo_z \cdot E \qquad (I)$$

wherein $SiO_x$ represents silicon oxide

Org represents at least one non-hydrolysable organic constituent

SiH represents the molar proportion of SiH units $TiO_{y'}$ represents titanium dioxide, $MoO_{y''}$ represents molybdenum oxide M represents a promoter, E represents at least one precious metal, and x, y', y" and z represent the number of oxygen atoms needed to satisfy the valencies of the organic-inorganic and/or purely inorganic elements Si, Ti, Mo and M, wherein more than 50% of the precious metal in the support has a diameter in the range of from 0.01 to 10 nm.

2. The precious metal-containing support according to claim 1, wherein the amount of Org is between 5 and 200 mole %, based on the amount of silicon oxide.

3. The precious metal-containing support according to claim 1, wherein the amount of SiH is between 0.01 and 100 mole %, based on the amount of silicon oxide.

4. The precious metal-containing support according to claim 1, wherein the amount of titanium oxide is between 0.3 and 20 mole %, based on the amount of silicon oxide.

5. The precious metal-containing support according to claim 1, wherein the amount of molybdenum oxide is between 0.05 and 20 mole %, based on the amount of silicon oxide.

6. The precious metal-containing support according to claim 1, wherein the amount of E is between 0.001 and 20 wt. % of the composition.

7. The precious-metal containing support of claim 1, wherein the precious metal-containing support has catalytic activity.

8. A process for the partial oxidation of a hydrocarbon in the presence of the precious-metal containing support of claim 1, molecular oxygen, hydrogen, and optionally, other gases.

9. The process according to claim 8, wherein the hydrocarbon is propene.

10. The process according to claim 9, where propene is oxidized to propene oxide.

11. A process for preparing a precious metal-containing support comprising:

(a) bringing
    (i) at least one support material comprising free SiH groups into contact with
    (ii) at least one precious metal compound and/or at least one precious metal particle for up to two hours to form a precious metal-containing support wherein the precious metal on the precious metal-containing support has a diameter in the range of from 0.01 to 10 nm; and (b) drying the precious metal-containing support by a spray drying process or by a fluidized bed process.

12. The process according to claim 11, wherein the at least one support material comprises an organic-inorganic hybrid material.

13. The process according to claim 11, wherein the at least one precious metal compound and/or the at least one precious metal particle is selected from the group consisting of gold, silver, palladium, platinum, ruthenium and mixtures thereof.

14. The process according to claim 11, wherein the contact time is less than 0.5 hour.

15. The process according to claim 11, wherein the at least one support material is thermally treated before and/or after contact with the at least one precious metal compound and/or the at least one precious metal particle.

16. The precious metal-containing support according to claim 1, wherein the promoter comprises at least one oxide of Ta, Fe, Sb, V, Nb, Zr, Al, B, Y and Ge.

17. The precious metal-containing support according to claim 1, wherein E comprises at least one of gold, silver, palladium, platinum and ruthenium.

* * * * *